United States Patent
Zhu et al.

(10) Patent No.: US 9,598,368 B2
(45) Date of Patent: Mar. 21, 2017

(54) PROCESS FOR THE PREPARATION OF 4-AMINO-3-CHLORO-5-FLUORO-6-(SUBSTITUTED)PICOLINATES

(71) Applicants: Yuanming Zhu, Carmel, IN (US); Gregory T. Whiteker, Carmel, IN (US); Cynthia Arndt, Carmel, IN (US); James M. Renga, Indianapolis, IN (US); Robert D. J. Froese, Midland, MI (US)

(72) Inventors: Yuanming Zhu, Carmel, IN (US); Gregory T. Whiteker, Carmel, IN (US); Kim E. Arndt, Carmel, IN (US); James M. Renga, Indianapolis, IN (US); Robert D. J. Froese, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/049,645

(22) Filed: Oct. 9, 2013

(65) Prior Publication Data

US 2014/0046070 A1    Feb. 13, 2014

Related U.S. Application Data

(62) Division of application No. 13/356,675, filed on Jan. 24, 2012, now Pat. No. 8,609,853.

(60) Provisional application No. 61/435,974, filed on Jan. 25, 2011.

(51) Int. Cl.
 C07D 213/79      (2006.01)
 C07D 213/84      (2006.01)
 C07D 213/803     (2006.01)
 C07D 213/807     (2006.01)

(52) U.S. Cl.
 CPC ....... $C07D$ $213/807$ (2013.01); $C07D$ $213/79$ (2013.01); $C07D$ $213/803$ (2013.01); $C07D$ $213/84$ (2013.01)

(58) Field of Classification Search
 None
 See application file for complete search history.

(56) References Cited

U.S. PATENT DOCUMENTS

| | | |
|---|---|---|
| 3,755,338 A | 8/1973 | Gulbenk |
| 3,971,799 A | 7/1976 | McGregor |
| 4,087,431 A | 5/1978 | McGregor |
| 4,814,456 A | 3/1989 | Michael |
| 4,999,432 A | 3/1991 | Friese et al. |
| 5,710,106 A | 1/1998 | Kleemann et al. |
| 6,297,197 B1 | 10/2001 | Fields et al. |
| 6,392,084 B1 | 5/2002 | Kaieda et al. |
| 6,784,137 B2 | 8/2004 | Balko et al. |
| 7,314,849 B2 | 1/2008 | Balko et al. |
| 7,432,227 B2 | 10/2008 | Balko et al. |
| 7,498,468 B2 | 3/2009 | Balko et al. |
| 2001/0047099 A1 | 11/2001 | Fields et al. |
| 2008/0051405 A1 | 2/2008 | Giordanetto et al. |
| 2008/0051596 A1 | 2/2008 | Balko et al. |
| 2011/0114097 A1 | 5/2011 | Schnell |
| 2011/0195930 A1 | 8/2011 | Haga et al. |

FOREIGN PATENT DOCUMENTS

EP    1498413 B1    8/2011

*Primary Examiner* — Zinna Northington Davis
(74) *Attorney, Agent, or Firm* — Michael R. Asam

(57) ABSTRACT

4-Amino-3-chloro-5-fluoro-6-(substituted)picolinates are conveniently prepared from 3,4,5,6-tetrachloropicolinonitrile by a series of steps involving fluorine exchange, amination, reaction with hydrazine, halogenation, hydrolysis and esterification, and transition metal assisted coupling.

3 Claims, No Drawings

PROCESS FOR THE PREPARATION OF 4-AMINO-3-CHLORO-5-FLUORO-6-(SUBSTITUTED)PICOLINATES

CROSS REFERENCE TO RELATED APPLICATIONS

This application is a divisional of U.S. patent application Ser. No. 13/356,675 filed Jan. 24, 2012, which claims the benefit of U.S. Provisional Patent Application Ser. No. 61/435,974 filed Jan. 25, 2011.

FIELD OF THE INVENTION

The present invention concerns a process for the preparation of 4-amino-3-chloro-5-fluoro-6-(substituted)picolinates. More particularly, the present invention concerns a process for the preparation of 4-amino-3-chloro-5-fluoro-6-(substituted)picolinates in which the 5-fluoro substituent is introduced by a halogen exchange early in the process scheme.

BACKGROUND OF THE INVENTION

U.S. Pat. No. 6,297,197 B1 describes inter alia certain 4-amino-3-chloro-5-fluoro-6-(alkoxy or aryloxy)picolinate compounds and their use as herbicides. U.S. Pat. Nos. 6,784,137 B2 and 7,314,849 B2 describe inter alia certain 4-amino-3-chloro-5-fluoro-6-(aryl)picolinate compounds and their use as herbicides. U.S. Pat. No. 7,432,227 B2 describes inter alia certain 4-amino-3-chloro-5-fluoro-6-(alkyl)picolinate compounds and their use as herbicides. Each of these patents describes the manufacture of 4-amino-3-chloro-5-fluoropicolinate starting materials by fluorination of the corresponding 5-unsubstituted picolinates with 1-(chloromethyl)-4-fluoro-1,4-diazoniabicyclo[2.2.2]octane bis(tetrafluoroborate). It would be advantageous to produce 4-amino-3-chloro-5-fluoro-6-(substituted)picolinates without having to rely on direct fluorination of the 5-position of the picolinate with an expensive fluorinating agent like 1-(chloromethyl)-4-fluoro-1,4-diazoniabicyclo[2.2.2]octane bis(tetrafluoroborate).

SUMMARY OF THE INVENTION

The present invention concerns a process for the preparation of 4-amino-3-chloro-5-fluoro-6-(substituted)picolinates from 3,4,5,6-tetrachloropicolinonitrile. More particularly, the present invention concerns a process for the preparation of a 4-amino-3-chloro-5-fluoro-6-(substituted)picolinate of the Formula I

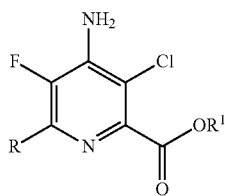

wherein
R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and
$R^1$ represents $C_1$-$C_{12}$ alkyl or an unsubstituted or substituted $C_7$-$C_{11}$ arylalkyl;
which comprises the following steps:

a) fluorinating 3,4,5,6-tetrachloropicolinonitrile (Formula A)

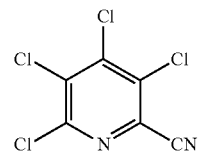

with a source of fluoride ion to produce 3-chloro-4,5,6-trifluoropicolinonitrile (Formula B)

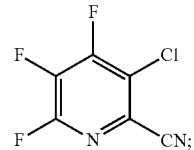

b) aminating 3-chloro-4,5,6-trifluoropicolinonitrile (Formula B) with ammonia to produce 4-amino-3-chloro-5,6-difluoropicolinonitrile (Formula C)

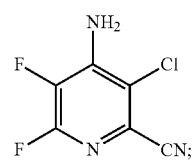

c) reacting the fluoro substituent in the 6-position of 4-amino-3-chloro-5,6-difluoropicolinonitrile (Formula C) with hydrazine to produce 4-amino-3-chloro-5-fluoro-6-hydrazinopicolinonitrile (Formula D)

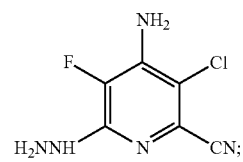

d) halogenating 4-amino-3-chloro-5-fluoro-6-hydrazinopicolinonitrile (Formula D) with a chlorine, bromine or iodine source to produce a 4-amino-3-chloro-5-fluoro-6-halopicolinonitrile of Formula E

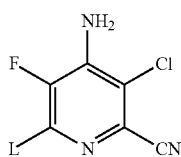

E wherein L is Br, Cl or I;

e) hydrolyzing and esterifying the 4-amino-3-chloro-5-fluoro-6-halopicolinonitrile of Formula E with a strong acid and an alcohol ($R^1OH$) to produce a 4-amino-3-chloro-5-fluoro-6-halopicolinate of Formula F

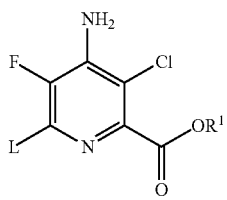

F wherein L and $R^1$, are as previously defined; and f) coupling the 4-amino-3-chloro-5-fluoro-6-halopicolinate of Formula F with an aryl, alkyl or alkenyl metal compound of the Formula G R-Met    G wherein R is as previously defined and Met represents, Zn-halide, Zn—R, tri-($C_1$-$C_4$ alkyl)tin, copper, or $B(OR^2)(OR^3)$, where $R^2$ and $R^3$ are independent of one another, hydrogen, $C_1$-$C_4$ alkyl, or when taken together form an ethylene or propylene group in the presence of a transition metal catalyst to produce the 4-amino-3-chloro-5-fluoro-6-(substituted)picolinate of Formula I.

The steps a) through f) may be performed in the order listed, as depicted in Scheme I, or some of the steps can be rearranged into different orders as allowed by the compatibility of the chemistry. For example, the coupling of step f) may be performed prior to the hydrolysis and esterification of step e).

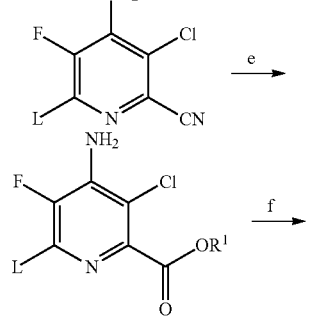

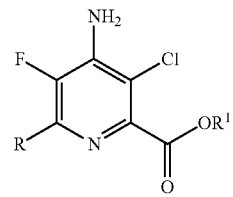

An additional aspect of the invention concerns an improved method of increasing the amount of recoverable 3-chloro-4,5,6-trifluoropicolinonitrile (Formula B)

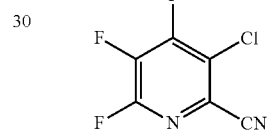

B prepared from fluorinating 3,4,5,6-tetrachloropicolinonitrile (Formula A)

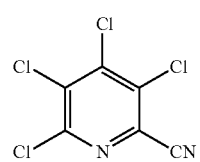

A with a source of fluoride ion wherein the improvement comprises the steps of:

i) isolating the over-fluorinated 3,4,5,6-tetrafluoropicolinonitrile (H)

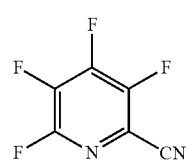

H by-product from fluorinating 3,4,5,6-tetrachloropicolinonitrile;

ii) reacting the isolated 3,4,5,6-tetrafluoropicolinonitrile (H) (a) with lithium chloride (LiCl), (b) with 3,4,5,6-tetrachloropicolinonitrile (Formula A) in the presence of a phase-transfer catalyst or (c) with a combination of LiCl and Scheme I

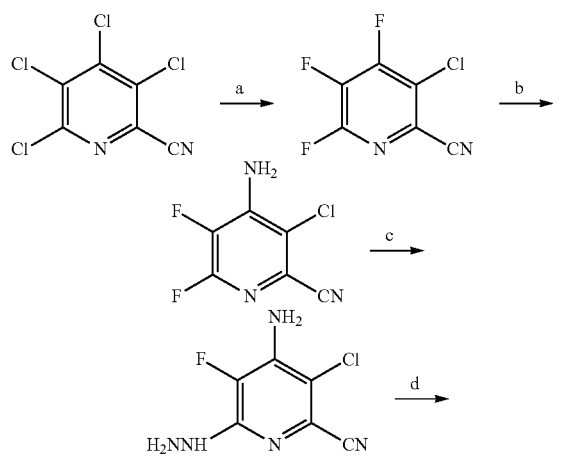

3,4,5,6-tetrachloropicolinonitrile to produce a mixture consisting predominantly of 3,4,5,6-tetrachloropicolinonitrile, monofluoro-trichloropicolinonitrile and difluoro-dichloropicolinonitrile; and iii) recycling the mixture consisting predominantly of 3,4,5,6-tetrachloropicolinonitrile, monofluoro-trichloropicolinonitrile and difluoro-dichloropicolinonitriles to the fluorination reaction preparing 3-chloro-4,5,6-trifluoropicolinonitrile (Formula B).

Another aspect of the present invention is the novel intermediate produced during the present process, viz., the compound:

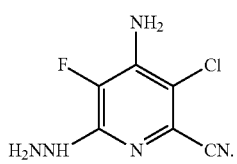

DETAILED DESCRIPTION OF THE INVENTION

The terms "alkyl," "alkenyl" and "alkynyl," as well as derivative terms such as "alkoxy," "acyl," "alkylthio" and "alkylsulfonyl," as used herein, include within their scope straight chain, branched chain and cyclic moieties. Unless specifically stated otherwise, each may be unsubstituted or substituted with one or more substituents selected from but not limited to halogen, hydroxy, alkoxy, alkylthio, $C_1$-$C_6$ acyl, formyl, cyano, aryloxy or aryl, provided that the substituents are sterically compatible and the rules of chemical bonding and strain energy are satisfied. The terms "alkenyl" and "alkynyl" are intended to include one or more unsaturated bonds.

The term "arylalkyl," as used herein, refers to a phenyl substituted alkyl group having a total of 7 to 11 carbon atoms, such as benzyl (—$CH_2C_6H_5$), 2-methylnaphthyl (—$CH_2C_{10}H_7$) and 1- or 2-phenethyl (—$CH_2CH_2C_6H_5$ or —$CH(CH_3)C_6H_5$). The phenyl group may itself be unsubstituted or substituted with one or more substituents independently selected from halogen, nitro, cyano, $C_1$-$C_6$ alkyl, $C_1$-$C_6$ alkoxy, halogenated $C_1$-$C_6$ alkyl, halogenated $C_1$-$C_6$ alkoxy, $C_1$-$C_6$ alkylthio, C(O)O$C_1$-$C_6$alkyl, or where two adjacent substituents are taken together as —O(CH$_2$)$_n$O— wherein n=1 or 2, provided that the substituents are sterically compatible and the rules of chemical bonding and strain energy are satisfied.

Unless specifically limited otherwise, the term "halogen," as well as derivative terms such as "halo," refers to fluorine, chlorine, bromine and iodine.

The phenyl groups substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy may be of any orientation, but 4-substituted phenyl, 2,4-disubstituted phenyl, 2,3,4-trisubstituted phenyl, 2,4,5-trisubstituted phenyl, and 2,3,4,6-tetrasubstituted phenyl isomers are preferred.

The 4-amino-3-chloro-5-fluoro-6-(substituted)picolinates are prepared from 3,4,5,6-tetrachloropicolinonitriles by a series of steps involving fluorine exchange, amination, reaction with hydrazine, halogenation, hydrolysis, esterification and transition metal assisted coupling. The individual steps may be performed in different sequences.

The 3,4,5,6-tetrachloropicolinonitrile starting material is a known compound and is commercially available.

In the fluoride exchange reaction, the fluorinated picolinonitrile is prepared by reacting the corresponding chlorinated picolinonitrile with approximately one equivalent of fluoride ion source for each ring chlorine substituent to be exchanged.

Typical fluoride ion sources are alkali metal fluorides which include sodium fluoride (NaF), potassium fluoride (KF) and cesium fluoride (CsF), with KF and CsF being preferred. Quaternary alkyl or aryl ammonium or phosphonium fluoride may also be used as a fluoride source or as an additive. Preferably, the reaction is carried out in a polar aprotic solvent or reaction medium such as, dimethylsulfoxide (DMSO), N-methylpyrrolidinone (NMP), N,N-dimethylformamide (DMF), hexamethylphosphoramide (HMPA) or sulfolane. The temperature at which the reaction is conducted is not critical but usually is from about 60° C. to about 180° C. and preferably from about 70° C. to about 80° C. Depending upon which solvent is employed in a particular reaction, the optimum temperature will vary. Generally speaking, the lower the temperature the slower the reaction will proceed. The present reaction is typically conducted in the presence of vigorous agitation sufficient to maintain an essentially uniformly dispersed mixture of the reactants.

In conducting the fluorination reaction, neither the rate nor the order of addition of the reactants is critical. Usually, the solvent and alkali metal fluoride are mixed before the chlorinated picolinonitrile is added to the reaction mixture. A typical reaction generally requires from about 2 to about 100 hours, preferably from 3 to 6 hours and is usually conducted at ambient atmospheric pressure.

While the exact amount of reactants is not critical, it is preferred to employ an amount of alkali metal fluoride which will supply at least an equimolar amount of fluorine atoms based on the number of chlorine atoms to be exchanged in the starting material, i.e., at least an equimolar amount of alkali metal fluoride. After the reaction is completed the desired product is recovered by employing standard separation and purification techniques such as distillation, crystallization or chromatography.

In a typical fluoride exchange, a mixture of products is obtained, including a significant amount of the over-fluorinated by-product 3,4,5,6-tetrafluoropicolinonitrile (Formula H).

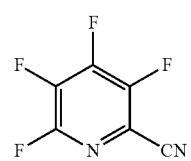

The ultimate yield of the desired 3-chloro-4,5,6-trifluoropicolinonitrile can be enhanced by isolating the over-fluorinated by-product 3,4,5,6-tetrafluoropicolinonitrile and recycling it to produce intermediates that can be subjected to the fluoride exchange reaction. This can be accomplished in several ways. Reaction of 3,4,5,6-tetrafluoropicolinonitrile with LiCl or reaction of 3,4,5,6-tetrafluoropicolinonitrile with an excess of 3,4,5,6-tetrachloropicolinonitrile or a combination of both, with or without solvents, leads to mixtures of chloro-fluoropicolinonitriles where the 3-chloro isomers are useful as a starting material to form the desired product. Thus 3,4,5,6-tetrafluoropicolinonitrile can be heated with excess LiCl to produce a mixture of predominately 3,4,5-trichloro-6-fluoropicolinonitrile and tetrachloropicolinonitrile. In another technique, reaction of the isolated 3,4,5,6-tetrafluoropicolinonitrile with an excess of 3,4,5,6-tetrachloropicolinonitrile in the presence of a phase-transfer catalyst produces a mixture consisting predominantly of monofluoro-trichloropicolinonitriles and difluoro-dichloropicolinonitriles. Finally, equal mixtures of isolated 3,4,5,6-tetrafluoropicolinonitrile and 3,4,5,6-tetrachloropicolinonitrile in the presence of a phase-transfer catalyst and from about 1 to about 3 equivalents of LiCl produces a mixture of predominately 3,4,5-trichloro-6-fluoropicolinonitrile and 3,4,5,6-tetrachloropicolinonitrile. These mixtures, consisting predominantly of monofluoro-trichloropicolinonitriles and/or difluoro-dichloropicolinonitriles, are useful in a fluorination reaction using an alkali metal fluoride to prepare 3-chloro-4,5,6-trifluoropicolinonitrile from 3,4,5,6-tetrafluoropicolinonitrile.

In a reverse halogen exchange reaction, 3,4,5,6-tetrafluoropicolinonitrile is heated with from about 5 to about 10 equivalents of LiCl, preferably with about 6 equivalents to produce a mixture of 4,5-dichloro-3,6-difluoropicolinonitrile (3,6-$F_2$—PN), 6-fluoro-3,4,5-trichloropicolinonitrile (6-F—PN) and 3,4,5,6-tetrachloropicolinonitrile ($Cl_4$—PN). The reaction can be carried out neat or in a polar aprotic solvent or reaction medium such as, DMSO, NMP, DMF, HMPA or sulfolane. It is often convenient to conduct the reaction in a solvent. The temperature at which the reaction is conducted is not critical but usually is from about 80° C. to about 200° C. and preferably from about 100° C. to about 150° C.

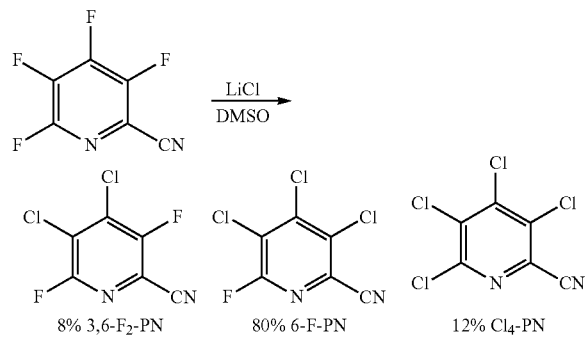

About 90% or more of the mixture is useful to form 3-chloro-4,5,6-trifluoropicolinonitrile by recycling the mixture through the fluorine exchange reaction.

In the metathesis reaction in which fluoro and chloro groups are interchanged, the 3,4,5,6-tetrafluoropicolinonitrile is reacted with from 1 to about 3 equivalents of 3,4,5,6-tetrachloropicolinonitrile, preferably with about 2 equivalents of 3,4,5,6-tetrachloropicolinonitrile. The reaction can be carried out neat or in a polar aprotic solvent or reaction medium such as, DMSO, NMP, DMF, HMPA or sulfolane. It is often convenient to conduct the reaction without a solvent. The metathesis reaction is conducted in the presence of an additive. Additives include (a) quaternary phosphonium salts containing 10 or more carbon atoms and (b) macrocyclic polyethers commonly known as crown ethers. Suitable crown ether catalysts include, but are not limited to, 18-crown-6; dicyclohexano-18-crown-6; dibenzo-18-crown-6; 15-crown-S. Suitable quaternary phosphonium salts include the tetra-n-alkylphosphonium salts which are especially preferred. The temperature at which the reaction is conducted is not critical but usually is from about 80° C. to about 200° C. and preferably from about 150° C. to about 180° C.

In a typical metathesis reaction, for example, in which 1 equivalent of 3,4,5,6-tetrafluoropicolinonitrile is allowed to react with about 2 equivalents of 3,4,5,6-tetrachloropicolinonitrile, the following mixture of isomers can be obtained: 3,4,5,6-tetrachloropicolinonitrile ($Cl_4$—PN), 3,5-dichloro-4,6-difluoropicolinonitrile (4,6-$F_2$—PN), 3,4-dichloro-5,6-difluoropicolinonitrile (5,6-$F_2$—PN), 4,5-dichloro-3,6-difluoropicolinonitrile (3,6-$F_2$—PN), 6-fluoro-3,4,5-trichloropicolinonitrile (6-F—PN) and 4-fluoro-3,5,6-trichloropicolinonitrile (4-F—PN).

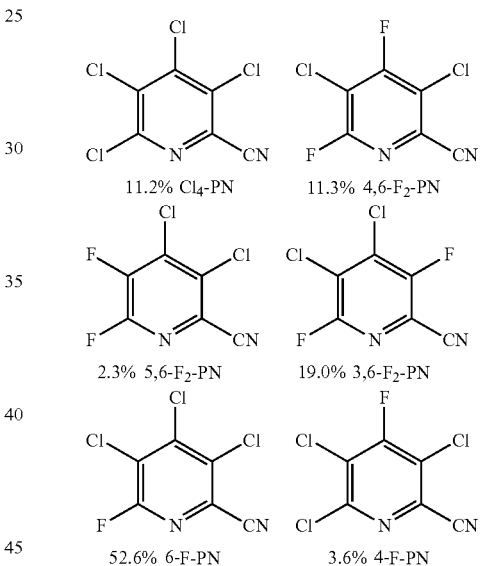

About 80% of the mixture is useful to form 3-chloro-4,5,6-trifluoropicolinonitrile by recycling the mixture through the fluorine exchange reaction.

In the combination of reverse halogen exchange reaction and the metathesis reactions, the 3,4,5,6-tetrafluoropicolinonitrile is allowed to react with from 1 to about 3 equivalents of 3,4,5,6-tetrachloropicolinonitrile, preferably with about 1 equivalent of 3,4,5,6-tetrachloropicolinonitrile and with from about 1 to about 4 equivalents of LiCl, preferably with from about 1.5 to about 2.5 equivalents. The reaction can be carried out neat or in a polar aprotic solvent or reaction medium such as, DMSO, NMP, DMF, HMPA or sulfolane. It is often convenient to conduct the reaction without a solvent. The metathesis reaction is conducted in the presence of an additive. Additives include (a) quaternary phosphonium salts containing 10 or more carbon atoms and (b) macrocyclic polyethers commonly known as crown ethers. Suitable crown ether catalysts include, but are not limited to, 18-crown-6; dicyclohexano-18-crown-6; dibenzo-18-crown-6; 15-crown-S. Suitable quaternary phosphonium salts include the tetra-n-alkylphosphonium salts which are especially preferred. The temperature at which the reaction is conducted is not critical but usually is from about 80° C. to about 200° C. and preferably from about 150° C. to about 180° C.

In a typical combination of the reverse halogen exchange and metathesis reactions, for example, 1 equivalent of 3,4,5,6-tetrafluoropicolinonitrile is allowed to react with about 1 equivalent of 3,4,5,6-tetrachloropicolinonitrile and 1.5 equivalents of LiCl, and the following mixture of isomers can be obtained:

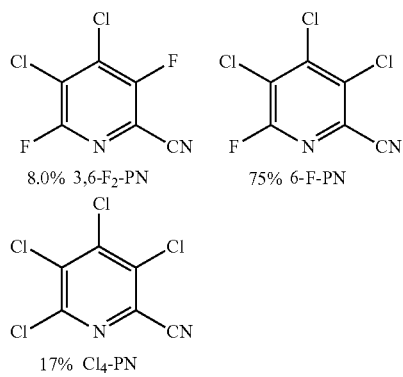

About 92% of the mixture is useful to form 3-chloro-4,5,6-trifluoropicolinonitrile by recycling the mixture through the fluorine exchange reaction.

In the amination reaction, the 4-fluoropicolinonitrile is allowed to react with ammonia to replace the fluorine atom with an amino group.

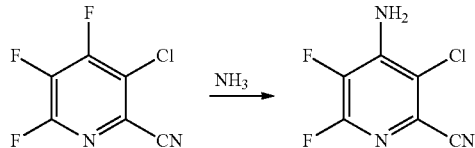

While only a stoichiometric amount of ammonia is required, it is often convenient to use a large excess of ammonia. It is often convenient to use the ammonia as both the reactant and the base to neutralize the hydrogen fluoride (HF) produced in the reaction. Alternatively, the ammonia can be in solution form, such as an aqueous solution of ammonium hydroxide. The reaction is carried out without a solvent or in an inert solvent. If a solvent is used, inert solvents include, but are not limited to, alcohols, ethers, esters, ketones, DMSO and aromatic solvents. The temperature at which the reaction is conducted is not critical but usually is from about 0° C. to about 45° C. and preferably from about 10° C. to about 30° C.

A typical reaction generally requires from about 0.5 to about 5 hours and is usually conducted at ambient atmospheric pressure. The desired product is recovered by employing standard separation and purification techniques.

In the reaction with hydrazine, the 6-fluoropicolinonitrile is allowed to react with hydrazine to replace the fluorine atom with a hydrazino group.

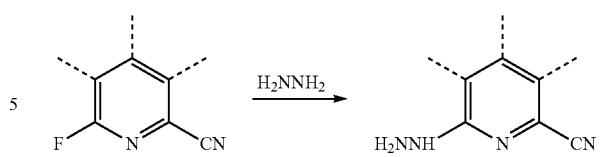

While only a stoichiometric amount of hydrazine is required, it is often convenient to use an excess of the hydrazine as both a reactant and as a base to neutralize the HF formed in the reaction. The hydrazine is preferably the monohydrate. The reaction is carried out in an inert polar solvent such as DMSO, DMF, NMP, acetonitrile, a chlorinated solvent, an ether, tetrahydrofuran (THF) or an alcohol. A mixture of DMSO and THF is preferred. The temperature at which the reaction is conducted is not critical but usually is from about ambient temperature to about 150° C. and preferably from about 35° C. to about 70° C.

In conducting the reaction with hydrazine, the hydrazine is dissolved in the solvent and 6-fluoropicolinonitrile is added to the reaction mixture. A typical reaction generally requires from about 0.5 to about 5 hours and is usually conducted at atmospheric pressure. The desired product is recovered by employing standard separation and purification techniques. The compounds can be easily isolated by dilution of the reaction mixture with acetonitrile followed by filtration.

In the halogenation reaction, the 6-halopicolinonitrile is prepared by reacting the corresponding 6-hydrazinopicolinonitrile with at least one equivalent of a brominating, chlorinating or iodinating agent.

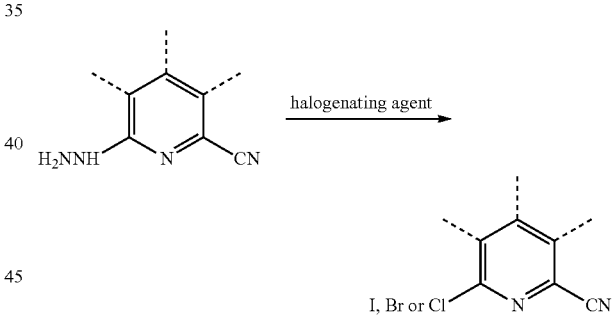

Suitable iodinating, chlorinating and brominating agents include but are not limited to iodine, iodine monochloride, chlorine, bromine, sulfuryl chloride and sulfuryl bromide. While only a stoichiometric amount of halogenating agent is required, it is often convenient to use an excess of the halogenating agent. The reaction is carried out in an inert aprotic solvent. A variety of solvents may be used such as chlorinated solvents, acetonitrile, DMSO, dioxane, DMF, and water. It is often preferable to use a chlorinated solvent. The temperature at which the reaction is conducted is not critical but usually is from about ambient temperature to about 100° C. and preferably from about ambient temperature to about 50° C.

In conducting the halogenation reaction, the 6-hydrazinopicolinonitrile is dissolved or suspended in the solvent and the halogenating agent is added to the reaction mixture. A typical reaction generally requires from about 0.5 to about 24 hours. The desired product is recovered by employing standard separation and purification techniques.

In the hydrolysis and esterification reactions, the picolinonitrile is allowed to react with an alcohol ($R^1OH$) in the presence of a Lewis or Bronsted acid.

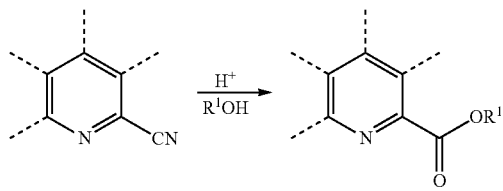

Bronsted acids include but are not limited to acids such as hydrochloric acid, sulfuric acid and phosphoric acid. Lewis acids include boron trifluoride, titanium tetrahalides, titanium tetraalkoxides, zinc halides, tin halides and phosphorus and antimony pentafluorides. Acids such as sulfuric acid or phosphoric acid are typically employed in stoichiometric amounts. The reaction is carried out in the $C_1$-$C_{12}$ alkyl alcohol or an unsubstituted or substituted $C_7$-$C_{11}$ arylalkyl alcohol of the desired ester. The reaction is conveniently conducted in a sealed reactor if the reaction temperature is above the boiling point of the alcohol solvent. In conducting the esterification, the picolinonitrile, or the hydrolysis intermediate picolinamide, is added to a mixture of the alcohol and acid. Although the temperature of the reaction is not critical, it is often heated to from about 80° C. to about 140° C. for about 2 to about 24 hours, preferably from about 100° C. to about 120° C. for about 6 to about 8 hours. The desired product is recovered by employing standard separation and purification techniques.

In the coupling reaction, a 6-halopicolinate is allowed to react with an aryl, alkyl or alkenyl metal compound where the metal is a Zn-halide, Zn—R, tri-($C_1$-$C_4$ alkyl)tin, copper, or $B(OR^2)(OR^3)$, where $R^2$ and $R^3$ are independent of one another, hydrogen, $C_1$-$C_4$ alkyl, or when taken together form an ethylene or propylene group, in the presence of a transition metal catalyst.

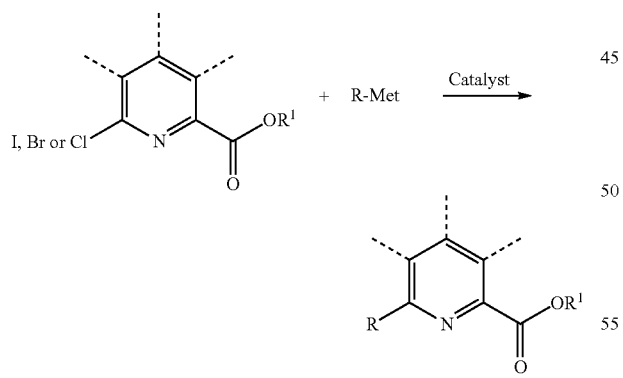

"Catalyst" is a transition metal catalyst, in particular a palladium catalyst such as palladium diacetate or dichlorobis(triphenylphosphine)palladium(II), or a nickel catalyst such as nickel(II) acetylacetonate or dichlorobis(triphenylphosphine)nickel(II). In addition, catalysts can be prepared in situ from metal salts and ligands, such as palladium(II) acetate and triphenylphosphine or nickel(II) chloride and triphenylphosphine. These in situ catalysts can be prepared by prior reaction of metal salt and ligand, followed by addition to the reaction mixture, or by separate addition of the metal salt and ligand directly to the reaction mixture.

Typically, coupling reactions are carried out in the absence of oxygen using an inert gas, such as nitrogen or argon. Techniques used to exclude oxygen from coupling reaction mixtures, such as sparging with inert gas, are well known to those skilled in the art. Examples of such techniques are described in *The Manipulation of Air-Sensitive Compounds*, $2^{nd}$ ed., D. F. Shriver, M. A. Drezdzon; Wiley-Interscience, 1986. Sub-stoichiometric amounts of a catalyst are used, typically from about 0.0001 equivalents to 0.1 equivalents. Additional amounts of ligand may optionally be added to increase catalyst stability and activity. In addition, additives such as sodium carbonate, potassium carbonate, potassium fluoride, cesium fluoride and sodium fluoride are typically added to the coupling reaction. The coupling reaction generally requires from about 1 to about 5 equivalents of such additive, preferably from 1 to 2 equivalents. Water may optionally be added to the coupling reaction to increase the solubility of these additives. The coupling reaction generally requires from about 1 to about 3 equivalents of an aryl, alkyl or alkenyl metal compound, preferably from 1 to 1.5 equivalents. The reaction is carried out in an inert solvent, such as toluene, THF, dioxane or acetonitrile. The temperature at which the reaction is conducted is not critical but usually is from about 25° C. to about 150° C. and preferably from about 50° C. to about 125° C. A typical reaction generally requires from about 0.5 to about 24 hours. No particular order of addition of reactants is typically required. It is often operationally simpler to combine all reactants except the catalyst and then deoxygenate the reaction solution. Following deoxygenation, the catalyst can be added to commence the coupling reaction.

When the Met portion of the aryl, alkyl or alkenyl metal compound is a Zn-halide, Zn—R or copper, protection of reactive functional groups may be necessary. For example, if an amino substituent (—NHR or —$NH_2$) is present, protection of these reactive groups may be required. A variety of groups are known in the art for protection of amino groups from reaction with organometallic reagents. Examples of such protecting groups are described in *Protective Groups in Organic Synthesis*, $3^{rd}$ ed., T. W. Greene, P. G. M. Wuts, Eds.; Wiley-Interscience, 1999. The choice of which metal to use in R-Met is influenced by a number of factors, such as cost, stability, reactivity and the need to protect reactive functional groups.

The products obtained by any of these processes, can be recovered by conventional means, such as evaporation or extraction, and can be purified by standard procedures, such as by recrystallization or chromatography.

The following examples are presented to illustrate the invention.

EXAMPLES

Fluorine Exchange

Example 1a

3-Chloro-4,5,6-trifluoropicolinonitrile

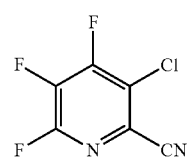

A 5-liter (L) mechanically stirred flask under nitrogen was charged with DMSO (3820 milliliters (mL)), powdered potassium carbonate ($K_2CO_3$; 42 grams (g)) and finely milled cesium fluoride (CsF; 1510 g). DMSO (approximately 1 L) was removed by distillation at 75-80° C. (3.5 mmHg, 0.46 kPa). The slurry was cooled to 55° C. under nitrogen before the addition of finely milled 3,4,5,6-tetrachloropicolinonitrile (685 g). The addition was conducted over a 15 minute (min) period while cooling to keep the reaction temperature below 74° C. The temperature was held at 65-70° C. under a slow nitrogen stream for 4 hours (h). The reaction mixture was cooled to about 40-50° C. and poured into a mixture of ice water ($H_2O$; 15 L) and diethyl ether ($Et_2O$; 3 L). After the organic phase was separated, the aqueous phase was extracted with $Et_2O$ (2×2 L). The organic extracts were combined, dried over magnesium sulfate ($MgSO_4$), filtered and concentrated by distillation at atmospheric pressure to give the crude product mixture (469 g) as light brown oil. This oil was combined with additional material prepared similarly to give a total of 1669 g of crude product. This oil was distilled under vacuum using a 30 tray Oldershaw column at a temperature range between 80-90° C. with fractions collected at 63, 13 and 2 mm Hg (8.4, 1.7 and 0.27 kPa). The material collected at 13 mm gave 457 grams (22% yield) of a solid that was a 93/7 mixture of two chlorotrifluoropicolinonitriles. This solid was recrystallized at 5° C. from a mixture of hexane (420 g) and $Et_2O$ to give 3-chloro-4,5,6-trifluoropicolinonitrile (354 grams, 98% purity) as fine white needles. A small sample was recrystallized a second time to 99.7% purity by gas chromatography (GC): mp 41.5-43° C.; $^{19}F$ NMR (376 MHz, $CDCl_3$) δ -78.1 (t, $J_{F-F}$=23.1 Hz, F6), -114.2 (dd, $J_{F-F}$=18.5, 22.5 Hz, F4), -149.3 (dd, $J_{F-F}$=18.2, 22.6 Hz, F5); $^{13}C\{^1H\}$ NMR (101 MHz, $CDCl_3$) δ 154.5 (ddd, $J_{F-C}$=270, 11, 7 Hz, C4), 151.3 (ddd, $J_{F-C}$=247, 13, 5 Hz, C6), 138.0 (ddd, $J_{F-C}$=279, 31, 13 Hz, C5), 124.7 (ddd, $J_{F-C}$=16, 6, 2 Hz, C3), 124.4 (ddd, $J_{F-C}$=16, 7, 2 Hz, C2), 112.2 (s, CN); EIMS m/z 192 ([M]$^+$). Anal. Calcd for $C_6ClF_3N_2$: C, 37.43; N, 14.55. Found: C, 36.91; N, 14.25.

The first part of the distillation (63 mm Hg, 8.4 kPa) gave pure 3,4,5,6-tetrafluoropicolinonitrile (525 g, 24%) as a colorless oil: $^{19}F$ NMR (376 MHz, $CDCl_3$) δ -77.6 (t, $J_{F-F}$=23.8 Hz, F6), -133.7 (q, $J_{F-F}$=18.8 Hz, F4), -134.2 (ddd, $J_{F-F}$=24.2, 18.6, 10.1 Hz, F3), -145.3 (ddd, $J_{F-F}$=24.1, 18.2, 10.2 Hz, F5); $^{13}C\{^1H\}$ NMR (101 MHz, $CDCl_3$) δ 150.4 (dm, $J_{F-C}$=272 Hz, C3), 148.5 (ddd, $J_{F-C}$=245, 12, 4 Hz, C6), 147.3 (dm, $J_{F-C}$=270 Hz, C4), 138.6 (ddd, $J_{F-C}$=280, 33, 11 Hz, C5), 113.4 (m, C2), 110.20 (s, CN).

The third part of the distillation (2 mm Hg, 0.27 kPa) gave 3,5-dichloro-4,6-difluoropicolinonitrile (48 g, 98% purity) as a white solid: mp 78-79° C.; $^{19}F$ NMR (376 MHz, $CDCl_3$) δ -63.65 (d, $J_{RF}$=18.7 Hz, F6), -92.52 (d, $J_{F-F}$=18.5 Hz, F4); $^{13}C\{^1H\}$ NMR (101 MHz, $CDCl_3$) δ 162.6 (dd, $J_{F-C}$=269, 6 Hz, C4), 157.8 (dd, $J_{F-C}$=245, 5 Hz, C6), 127.6 (dd, $J_{F-C}$=17, 3 Hz, C3), 123.5 (dd, $J_{F-C}$=18, 6 Hz, C2), 112.4 (dd, $J_{F-C}$=36, 21 Hz, C5), 112.3 (CN).

Example 1b

Reverse Halogen Exchange Reaction of 3,4,5,6-tetrafluoropicolinonitrile with Lithium Chloride

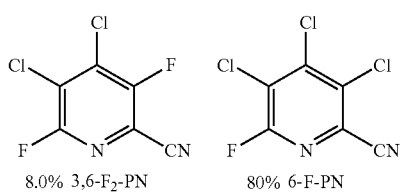

8.0% 3,6-$F_2$-PN     80% 6-F-PN

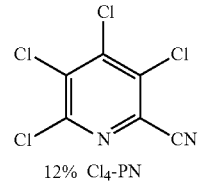

12% $Cl_4$-PN

A mixture of 3,4,5,6-tetrafluoropicolinonitrile (17 g, 0.1 mole (mol)) and dry LiCl (25.4 g, 0.6 mol) was heated in dry DMSO (200 mL). The reaction was monitored by GC analysis of aliquots extracted into $Et_2O$ from $H_2O$. Initially the reaction was heated to 120° C. and all of the LiCl dissolved. After 5 min at 120° C., all of the starting material and the chlorotrifluoro-PN isomers were consumed to give a mixture of 3,6-$F_2$—PN (83%) and 6-F—PN (14%). The temperature of the reaction was raised to 135° C. and after a total of 75 min was analyzed by GC. The mixture was determined to be a 8:80:12 mixture of 3,6-$F_2$—PN/6-F—PN/$Cl_4$—PN.

Example 1ca

Metathesis of 3,4,5,6-tetrafluoropicolinonitrile

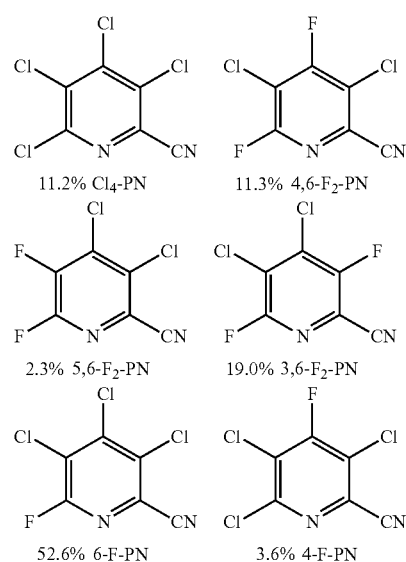

11.2% $Cl_4$-PN     11.3% 4,6-$F_2$-PN 2.3% 5,6-$F_2$-PN     19.0% 3,6-$F_2$-PN 52.6% 6-F-PN     3.6% 4-F-PN

A mixture of 3,4,5,6-tetrachloropicolinonitrile (16.1 g, 66 millimoles (mmol)) and 3,4,5,6-tetrafluoropicolinonitrile (5.9 g, 33 mmol) were heated to 160° C. under nitrogen to form a solution. To this stirred solution was added tetrabutyl phosphonium chloride ($Bu_4PCl$; 0.36 g, 1.2 mmol), and the solution was held at 160° C. for 1 h. An aliquot was dissolved in methylene chloride ($CH_2Cl_2$) and passed through a short pad of silica gel before GC analysis. The profile of halogenated picolinonitriles was: 11.2% $Cl_4$—PN; 11.3% 4,6-$F_2$—PN; 2.3% 5,6-$F_2$—PN; 19% 3,6-$F_2$—PN; 52.6% 6-F—PN and 3.6% 4-F—PN. About 80% of the mixture is useful in the halogen exchange reaction to produce 3-chloro-4,5,6-trifluoropicolinonitrile.

Example 1cb

Recycle from Metathesis of 3,4,5,6-tetrafluoropicolinonitrile

A reaction flask fitted with a short path distillation head was charged with finely milled CsF (35.1 g, 0.23 mol) and dry DMSO (175 mL). The reactor was stirred and heated to 70-75° C. under vacuum (0.1 mm) until DMSO (75 mL) was distilled off. This slurry was cooled to 50° C. under nitrogen, and the molten reaction mixture from above (21.7 g) was added. The reaction mixture was heated to 70° C. for 2.5 h with good stirring. A diethyl ether extract of an aliquot added to water was checked by GC and found to contain: 61% 3,4,5,6-tetrafluoropicolinonitrile; 31% 3-chloro-4,5,6-trifluoropicolinonitrile; 3.4% 5-chloro-3,5,6-trifluoropicolinonitrile and 4.8% 3,5-dichloro-4,6-difluoropicolinonitrile. This compares favorably to a typical crude GC purity of 38-42% when a similar reaction is conducted starting with pure 3,4,5,6-tetrachloropicolinonitrile.

Example 1d

LiCl Assisted Metathesis of 3,4,5,6-tetrafluoropicolinonitrile

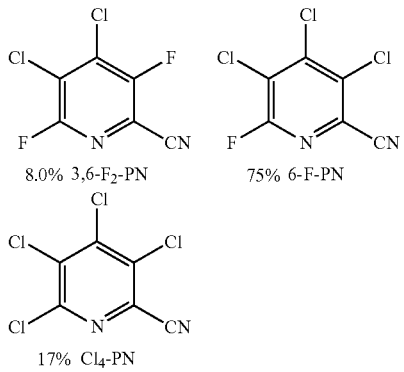

8.0% 3,6-F$_2$-PN    75% 6-F-PN

17% Cl$_4$-PN

A mixture of 3,4,5,6-tetrachloropicolinonitrile (12.2 g, 50 mmol) and 3,4,5,6-tetrafluoropicolinonitrile (8.8 g, 50 mmol) were heated to 160° C. under nitrogen to achieve a clear solution. To this was added Bu$_4$PCl (0.36 g, 1.2 mmol). The reaction solution was held at 160° C. for 15 min before adding dry LiCl (4.2 g, 0.1 mol). After 60 min more LiCl (2.2 g, 50 mmol) was added, and the reaction mixture was stirred for 11 h. GC analysis of an ether extract from water showed an 8:75:17 mixture of 3,6-F$_2$—PN/6-F—PN/Cl$_4$—PN.

Amination

Example 2

4-Amino-3-chloro-5,6-difluoropicolinonitrile

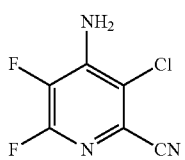 [SMILES: N#Cc1nc(F)c(F)c(N)c1Cl]

A solution of 3-chloro-4,5,6-trifluoropicolinonitrile (200 g) in ethyl acetate (EtOAc; 3 L) was cooled to 10° C. To this was slowly added 14% aqueous ammonium hydroxide (NH$_4$OH; 1296 g) keeping the temperature between 18-23° C. The aqueous solution was separated from the organic solution. The organic phase was washed sequentially with a 50/50 solution of aqueous saturated NaCl and water (500 mL) and saturated NaCl solution (250 mL). The organic phase was concentrated under vacuum at 50° C. to about 500 mL volume as the product crystallized out. To this slurry was added heptane (1 L), and the remaining EtOAc was removed under vacuum to give the final slurry. The solids were collected by filtration. This solid was washed with pentane and dried under vacuum to give 4-amino-3-chloro-5,6-difluoropicolinonitrile (173.8 g, 90%, 99.6% purity) as a white crystalline solid: mp 190-191.5° C.; $^{13}$C{$^1$H} NMR (101 MHz, DMSO-d$_6$) δ 150.03 (dd, J=232.4, 12.5 Hz, C6), 144.29 (dd, J=11.4, 6.9 Hz, C4), 133.72 (dd, J=257.9, 30.8 Hz, C5), 122.14 (dd, J=19.6, 4.9 Hz, C2), 119.31 (s, C3), 114.25 (s, CN); $^{19}$F NMR (376 MHz, DMSO-d$_6$) δ −91.24 (d, J=24.2 Hz), −154.97 (d, J=24.2 Hz); EIMS m/z 189 ([M]$^+$). Anal. Calcd for C$_6$H$_2$ClF$_2$N$_3$: C, 38.02; H, 1.06; N, 22.17. Found: C. 37.91; H, 1.00; 22.02.

Reaction with Hydrazine

Example 3

4-Amino-3-chloro-5-fluoro-6-hydrazinopicolinonitrile

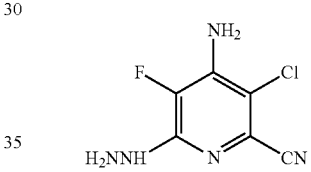

To a solution of hydrazine hydrate (3.9 g, 78 mmol) in THF (15 mL) and DMSO (10 mL) was added 4-amino-3-chloro-5,6-difluoropicolinonitrile (5 g, 26 mmol) as a solution in DMSO (5 mL). This solution was heated to 65° C. for 45 min, cooled and diluted with acetonitrile (30 mL) to precipitate the product as a light tan solid. This solid was dried under vacuum at 40° C. for 3 h to give 4-amino-3-chloro-5-fluoro-6-hydrazinopicolinonitrile (5.1 g, 98%): mp 215-220° C. dec; $^1$H NMR (400 MHz, DMSO-d$_6$) 7.9 (br, 1H), 6.5 (br, 2H), 4.0 (br, 2H); $^{13}$C {1H} NMR (101 MHz, DMSO-d$_6$) δ 149.34 (d, J=10.5 Hz, C6), 138.28 (d, J=11.6 Hz, C4), 133.81 (d, J=251.6 Hz, C5), 123.74 (d, J=5.3 Hz, C2), 115.87 (s, C3), 112.57 (s, CN); $^{19}$F NMR (376 MHz, DMSO-d$_6$) δ −154.6; ESIMS m/z 203 ([M+H]$^+$). Anal. Calcd for C$_6$H$_5$ClFN$_5$: C, 35.75; H, 2.50; N, 34.74. Found: C, 35.97; H, 2.70: N, 35.01.

Halogenation

Example 4

4-Amino-3,6-dichloro-5-fluoropicolinonitrile

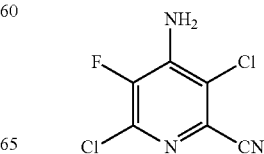

To a suspension of 4-amino-3-chloro-5-fluoro-6-hydrazinylpicolinonitrile (9.04 g, 44.8 mmol) in CH$_2$Cl$_2$ (150 mL) was added sulfuryl chloride (7.20 mL, 89 mmol). The mixture was stirred at room temperature for 40 h. The solvent was removed under reduced pressure, and the residue was partitioned with saturated aqueous sodium bicarbonate (NaHCO$_3$) and EtOAc. The organic phase was separated, dried over Na$_2$SO$_4$, and filtered. The solution was concentrated and the residue was purified by silica gel chromatography to give the product (7.01 g, 76%) as an off-white solid: $^1$H NMR (300 MHz, DMSO-d$_6$) δ 7.55 (s, 2H); $^{13}$C NMR (101 MHz, DMSO-d$_6$) δ 143.26 (d, J=259.2 Hz, C5), 142.69 (d, J=14.0 Hz, C4), 135.53 (d, J=17.6 Hz. C6), 126.07 (d, J=4.4 Hz, C2), 120.14 (d, J=4.3 Hz, C3), 114.36 (s, CN); $^{19}$F NMR (376 MHz, DMSO-d$_6$) δ −132.30 (s); ESIMS m/z 203 ([M+H]$^+$), 206.

Hydrolysis and Esterification

Example 5

Methyl 4-amino-3,6-dichloro-5-fluoropicolinate

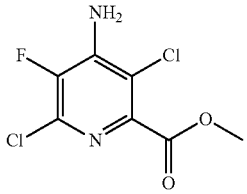

Concentrated sulfuric acid (2.0 mL, 37.5 mmol) was added slowly to methyl alcohol (8 mL) with cooling. Then 4-amino-3,6-dichloro-5-fluoropicolinonitrile (0.20 g, 0.97 mmol) was added to the solution, and the mixture was stirred at reflux for 29 h. The solvent was removed under vacuum, and the residue was poured into ice and stirred for 15 min. The product was extracted with EtOAc (3×). The organic extracts were combined, washed with brine, dried over MgSO$_4$, filtered, and purified by silica gel column to give methyl 4-amino-3,6-dichloro-5-fluoropicolinate (0.085 g, 37%) as a white solid: $^1$H NMR (400 MHz, CDCl$_3$) δ 5.08 (s, 2H), 3.97 (s, 3H); $^{13}$C NMR (101 MHz, CDCl$_3$) δ 163.57 (s, C=O), 143.29 (d, J=258.1 Hz, C5), 141.73 (d, J=5.1 Hz, C2), 141.05 (d, J=12.7 Hz, C4), 135.32 (d, J=16.8 Hz, C6), 116.26 (s, C3), 53.24 (s, OMe); $^{19}$F NMR (376 MHz, CDCl$_3$) δ −135.63 (s).

Coupling

Example 6a

Methyl 4-amino-3-chloro-5-fluoro-6-(4-chloro-2-fluoro-3-methoxyphenyl)picolinate

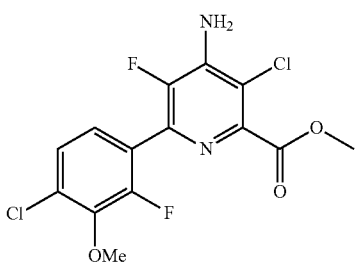 [SMILES: COC(=O)c1nc(-c2ccc(Cl)c(OC)c2F)c(F)c(N)c1Cl]

A 250 mL three-neck flask with a reflux condenser, a nitrogen inlet and a thermocouple was charged with methyl 4-amino-3,6-dichloro-5-fluoropicolinate (9.965 g, 41.7 mmol), 2-(4-chloro-2-fluoro-3-methoxyphenyl)-1,3,2-dioxaborinane (12.74 g, 52.1 mmol) and KF (4.84 g, 83 mmol). Acetonitrile (78 mL) and water (26 mL) were added. The reaction mixture was purged with nitrogen. Dichlorobis(triphenylphosphine)palladium(II) (Pd(PPh$_3$)$_2$Cl$_2$; 1.477 g, 2.10 mmol, 5 mol %) was added, and the solution was heated to 70° C. under nitrogen for 2 h. Upon cooling to room temperature, a precipitate formed which was filtered and washed with water. The precipitate was dissolved in EtOAc (ca 500 mL) and washed with water and then brine. The organic layer was dried (MgSO$_4$) and the solvent was removed using a rotary evaporator to give an orange solid, which was dried in vacuum oven at 50° C. (11.46 g, 76% yield): mp 169-170.5° C.; $^1$H NMR (400 MHz, DMSO-d$_6$) δ 7.48 (d, J=8.4 Hz, 1H), 7.32 (t, J=7.7 Hz, 1H), 7.15 (s, 2H), 3.96 (s, 3H), 3.90 (s, 3H); $^{13}$C{$^1$H} NMR (101 MHz, DMSO-d$_6$) δ 164.85 (s), 153.11 (d, J=252.5 Hz), 146.29 (s), 144.52 (d, J=4.3 Hz), 143.74 (s), 142.75 (dd, J=227.1, 14.0 Hz), 136.38 (d, J=13.4 Hz), 128.58 (d, J=3.2 Hz), 125.87 (s), 125.54 (d, J=3.5 Hz), 122.89 (dd, J=13.8, 4.0 Hz), 113.01 (d, J=3.0 Hz), 61.61 (d, J=4.2 Hz), 52.70 (s); ESIMS m/z 364 ([M+H]$^+$). Anal. Calcd for C$_{14}$H$_{10}$Cl$_2$F$_2$N$_2$O$_3$: C, 46.30; H, 2.78; N, 7.71. Found: C, 46.60; H, 2.68; N, 7.51.

Example 6b

4-Amino-3-chloro-5-fluoro-6-(4-chloro-2-fluoro-3-methoxyphenyl)picolinonitrile

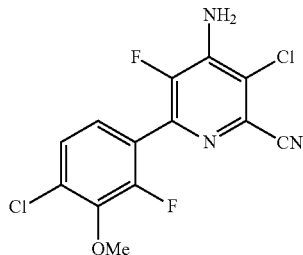 [SMILES: COc1c(Cl)ccc(-c2nc(C#N)c(Cl)c(N)c2F)c1F]

A mixture of 4-amino-3,6-dichloro-5-fluoropicolinonitrile (0.37 g, 1.80 mmol), 2-(4-chloro-2-fluoro-3-methoxyphenyl)-1,3,2-dioxaborinane (0.549 g, 2.24 mmol) and KF (0.209 g, 3.59 mmol) was taken into acetonitrile (6.75 mL) and water (2.25 mL). The mixture was stirred and sparged with a nitrogen atmosphere. Pd(PPh$_3$)$_2$Cl$_2$ (63 mg, 0.1 mmol) was added, and the mixture was again sparged with nitrogen. The solution was then heated to 75° C. under nitrogen for 2 h. Upon cooling down, a precipitate formed and was collected by filtration, washed with water and dried under vacuum to give the product (0.34 g) as an off-white solid. The aqueous phase was extracted with EtOAc (3×), and the combined organic extracts were washed with brine, dried, and concentrated. Purification by silica gel chromatography gave additional product (0.12 g) as a white solid. Total yield 78%. $^1$H NMR (400 MHz, DMSO-d$_6$) δ 7.50 (dd, J=8.5, 1.4 Hz, 1H), 7.45 (s, 2H), 7.33 (dd, J=8.5, 7.2 Hz, 1H), 3.94 (s, 3H); $^{13}$C {$^1$H} NMR (101 MHz, DMSO-d$_6$) δ 152.97 (d, J=253.2 Hz), 145.73 (d, J=260.8 Hz), 143.82 (d, J=13.7 Hz), 141.83 (d, J=14.7 Hz), 138.45 (d, J=14.8 Hz), 133.93-132.79 (m), 128.93 (d, J=3.3 Hz), 127.74 (s), 126.37-125.10 (m), 122.08 (dd, J=13.6, 3.9 Hz), 119.34 (d, J=4.5 Hz), 114.99 (s), 61.61 (s); $^{19}$F NMR (376 MHz, DMSO-$d_6$) δ −129.00 (dd, J=28.2, 7.0 Hz, 1F), −133.76 (d, J=28.2 Hz, 1F); ESIMS m/z 330.1 ([M+H]$^+$).

What is claimed is:

1. A process for the preparation of a 4-amino-3-chloro-5-fluoro-6-(substituted)picolinate of the Formula I

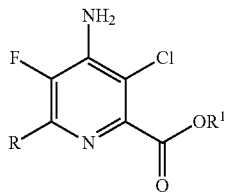

wherein
R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and
$R^1$ represents $C_1$-$C_{12}$ alkyl or an unsubstituted or substituted $C_7$-$C_{11}$ arylalkyl;
which comprises the following steps:
a) fluorinating 3,4,5,6-tetrachloropicolinonitrile (Formula A)

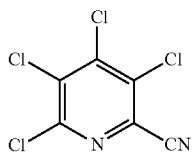

with a source of fluoride ion to produce 3-chloro-4,5,6-trifluoropicolinonitrile (Formula B)

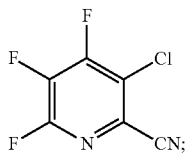

b) aminating 3-chloro-4,5,6-trifluoropicolinonitrile (Formula B) with ammonia to produce 4-amino-3-chloro-5,6-difluoropicolinonitrile (Formula C)

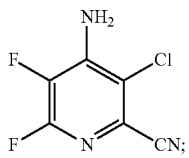

c) reacting the fluoro substituent in the 6-position of 4-amino-3-chloro-5,6-difluoropicolinonitrile (Formula C) with hydrazine to produce 4-amino-3-chloro-5-fluoro-6-hydrazinopicolinonitrile (Formula D)

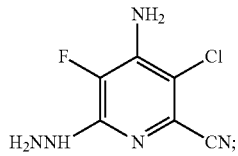

d) halogenating 4-amino-3-chloro-5-fluoro-6-hydrazinopicolinonitrile (Formula D) with a chlorine, bromine or iodine source to produce a 4-amino-3-chloro-5-fluoro-6-halopicolinonitrile of Formula E

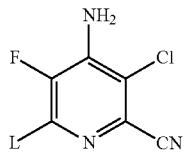

wherein L is Br, Cl or I;
e) hydrolyzing and esterifying the 4-amino-3-chloro-5-fluoro-6-halopicolinonitrile of Formula E with a strong acid and an alcohol ($R^1$OH) to produce a 4-amino-3-chloro-5-fluoro-6-halopicolinate of Formula F

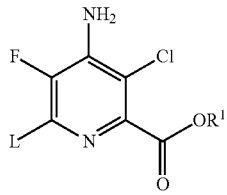

wherein L and $R^1$, are as previously defined; and
f) coupling the 4-amino-3-chloro-5-fluoro-6-halopicolinate of Formula F with an aryl, alkyl or alkenyl metal compound of the Formula G R-Met             G wherein R is as previously defined and Met represents, Zn-halide, Zn—R, tri-($C_1$-$C_4$ alkyl)tin, copper, or B(OR$^2$)(OR$^3$), where $R^2$ and $R^3$ are independent of one another, hydrogen, $C_1$-$C_4$ alkyl, or when taken together form an ethylene or propylene group in the presence of a transition metal catalyst to produce the 4-amino-3-chloro-5-fluoro-6-(substituted)picolinate of Formula I.

2. The process of claim 1 in which the coupling of step f) is performed prior to the hydrolysis and esterification of step e).

3. An improved process of increasing the amount of recoverable 3-chloro-4,5,6-trifluoropicolinonitrile (Formula B)

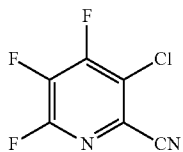

B

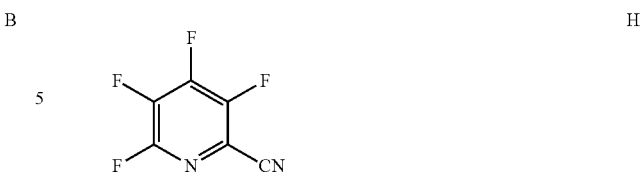

prepared from fluorinating 3,4,5,6-tetrachloropicolinonitrile (Formula A)

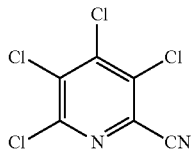

A with a source of fluoride ion wherein the improvement comprises the steps of:
  i) isolating the over-fluorinated 3,4,5,6-tetrafluoropicolinonitrile (H) by-product from fluorinating 3,4,5,6-tetrachloropicolinonitrile;
  ii) reacting the isolated 3,4,5,6-tetrafluoropicolinonitrile (H) (a) with lithium chloride (LiCl), (b) with 3,4,5,6-tetrachloropicolinonitrile (Formula A) in the presence of a phase-transfer catalyst or (c) with a combination of LiCl and 3,4,5,6-tetrachloropicolinonitrile to produce a mixture consisting predominantly of 3,4,5,6-tetrachloropicolinonitrile, monofluoro-trichloropicolinonitrile and difluoro-dichloropicolinonitrile; and
  iii) recycling the mixture consisting predominantly of 3,4,5,6-tetrachloropicolinonitrile, monofluoro-trichloropicolinonitrile and difluoro-dichloropicolinonitriles to the fluorination reaction preparing 3-chloro-4,5,6-trifluoropicolinonitrile (Formula B).

* * * * *